United States Patent [19]

Kornowski et al.

[11]  4,123,544
[45]  Oct. 31, 1978

[54] ACETYLSALICYLIC ACID DERIVATIVES

[75] Inventors: Henri Kornowski, Paris; Bernard Roques, St. Maurice; Robert Oberlin, Mantes LaVille; André Jondet, St. Mande, all of France

[73] Assignee: Merrell Toraude S. A., Paris, France

[21] Appl. No.: 773,564

[22] Filed: Mar. 2, 1977

[51] Int. Cl.² ............... C07D 207/12; A61K 31/40; C07D 207/16
[52] U.S. Cl. ............................. 424/274; 260/326.41
[58] Field of Search ............ 260/326.41, 326.46, 260/326.47, 480; 424/274

[56] References Cited

U.S. PATENT DOCUMENTS

| 2,101,867 | 12/1937 | Miller et al. | 260/480 |
| 2,764,614 | 9/1956 | Meyer | 260/480 |
| 3,518,297 | 6/1970 | Busacca | 260/480 |
| 3,793,366 | 2/1974 | Kropcho | 260/326.47 |

FOREIGN PATENT DOCUMENTS 1,220,447  1/1971  United Kingdom ............... 260/480

OTHER PUBLICATIONS

Morrison et al.; Organic Chemistry, 2nd Edition (1969) pp. 1100–1101.

Chem. Abs., vol. 46: 10161g (1952).
Chem. Abs., vol. 74: 125591c (1971).

Primary Examiner—Donald G. Daus
Assistant Examiner—Mary C. Vaughn
Attorney, Agent, or Firm—William J. Stein; Eugene O. Retter; George W. Rauchfuss, Jr.

[57]  ABSTRACT

This invention relates to acetylsalicylic acid derivatives of the formula

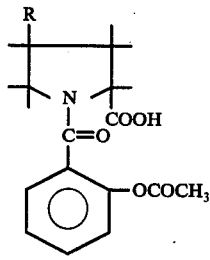

wherein R is H or OH, which have good analgesic, anti-inflammatory, and antipyretic activity and are, at the same time, free of ulcerogenic activity when administered orally.

2 Claims, No Drawings

ACETYLSALICYLIC ACID DERIVATIVES

The present invention is concerned with certain novel acetylsalicylic acid derivatives, with a process for their preparation, and with compositions containing them.

Acetylsalicylic acid and derivatives thereof with certain aminoacids are known and are used in the pharmaceutical field as analgesics, anti-inflammatory agents and antipyretic agents. It is a disadvantage of acetylsalicylic acid, however, that it is ulcerogenic when administered orally.

We have now found that acetylsalicylic acid derivatives of the formula:

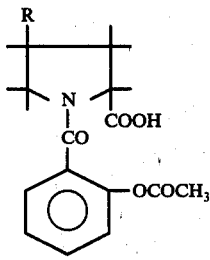

where R is H or OH, have good analgesic, anti-inflammatory and antipyretic activity and are, at the same time, free of ulcerogenic activity when administered orally.

The above formula covers two compounds, that is 1-o-acetoxybenzoyl-L-proline and 1-o-acetoxybenzoyl-4-hydroxyl-L-proline; these compounds are novel and constitute one aspect of the present invention.

The present invention also comprises a process for the preparation of the compounds according to the invention, which comprises reacting L-proline or 4-hydroxy-L-proline with acetylsalicylic acid or a halide thereof in a neutral or slightly basic aqueous organic medium, precipitating the desired compound by acidifying the medium, and recovering the precipitated compound.

The precipitated compound is preferably separated from the reaction medium by extraction with an organic solvent, such as ethyl acetate, methylene chloride or dichloroethane.

The reaction is preferably carried out in two stages, the first stage being at a low temperature of about $-2°$ C. and the second stage being at ambient temperature.

Suitable aqueous organic media are, for example, mixtures of water, triethylamine and ether.

The compounds according to the invention can be administered enterally or parenterally, preferably in a unit dose of from 100 mg to 1 g of active principle. The compound can be formulated, for example, as an injectable ampoule, a gelatine-coated pill or a tablet, or a suppository. For human patients, from one to five of such unit doses may be administered per day, for example, for the alleviation of neuralgias of rheumatic or other origin.

The absence of ulcerogenic activity in the compounds according to the invention is particularly valuable and can be demonstrated by a technique based on that described by A. Jondet (*Annales pharmaceutiques francaises*, 1968, No. 12, pages 767-770) which consists of bringing about the appearance of gastric ulcers in rats which are exposed to cold (with ingestion of the product to be tested or, for comparison, in the absence of any product).

In order that the invention may be more fully understood, the following examples are given by way of illustration only.

EXAMPLE 1

Preparation of 1-o-acetoxybenzoyl-4-hydroxy-L-proline 24.05 g (0.121 mol) of o-acetoxybenzoyl chloride in 50 ml of anhydrous ether, and 17 ml (0.121 mol) of pure triethylamine in 18 ml of iced water, were added simultaneously over the course of 0.5 hr, at $-2°$ C. $\pm$ 1° C., whilst stirring so as to produce emulsification, to a solution of 15.9 g (0.121 mol) of 4-hydroxy-L-proline in 42 ml of water and 17 ml (0.121 mol) of pure triethylamine. Stirring was continued for 0.75 hr at the same temperature and then for 25 minutes at ambient temperature. The pH was reduced from 7 to 3 by adding 9.8 ml of 12.35 N HCl (0.121 mol). The milky cloudiness was extracted with a total of 900 ml of pure ethyl acetate and the combined organic extracts were dried over anhydrous $Na_2SO_4$ and then concentrated in vacuo to give, in 2 to 3 successive crops, 23 g of the desired product (65% yield).

Quantitative analysis $C_{14}H_{15}NO_6 = 293.27$
Calculated % C = 57.33; H = 5.16; N = 4.78; O = 32.72
Found % C = 56.92; H = 5.06; N = 4.89; O = 33.54
Melting point: 175° C.
Solubility in water, about 5% by weight (pH = 3).
Specific optical rotation in water:

$$\alpha_D = -114°$$

EXAMPLE 2

Acute toxicity on intravenous administration to mice

The acute toxicity of 1-o-acetoxybenzoyl-4-hydroxy-L-proline was investigated by comparison with an injectable aspirin, namely lysine acetylsalicylate. The acetylsalicylic acid content of the two compounds was substantially the same (about 50%).

The results of the two experiments are shown in Table I below:

TABLE I

| (Intravenous administration to mice) | | |
|---|---|---|
| Dosage (0.5 ml/20 g) | 1-o-acetoxybenzoyl-4-hydroxy-L-proline | Injectable aspirin |
| 700 mg/kg | 0/5* | |
| 1,500 mg/kg | 0/5 | 0/5 |
| 2,000 mg/kg | | 5/5 |
| 3,000 mg/kg | 0/5 | 3/5 |
| 3,500 mg/kg | | 5/5 |
| 4,000 mg/kg | 0/5 | |

*x/5: number of dead animals amongst 5 animals tested.

In the case of injectable aspirin, the immediate symptoms were pronounced, with depression, ataxia and convulsions occurring. Death occurred from 30 minutes to 2 hours after administration.

In contrast, practically no symptoms were observed in the mice to which the compound according to the invention had been administered. The $LD_{50}$ of the compound according to the invention, when administered intraperitoneally to mice, was about 10g/kg, whilst it was about 3g/kg for lysine acetylsalicylate.

1-o-Acetoxybenzoyl-4-hydroxy-L-proline did not give rise to any toxic manifestations when administered orally to mice at the rate of 10g/kg, whilst lysine acetylsalicylate has an $LD_{50}$ of 3g/kg when administered by this route.

The results given in Table I show that 1-o-acetoxybenzoyl-4-hydroxy-L-proline is substantially non-toxic when administered to mice intravenously, whilst lysine acetylsalicylate has an $LD_{50}$ of about 2g/kg by this route.

EXAMPLE 3

Analgesic activity

The analgesic activity of 1-o-acetoxybenzoyl-4-hydroxy-L-proline was studied by means of the phenylbenzoquinone cramping test, in comparison with the same injectable aspirin as that used in Example 2, the two compouns being administered orally 2 hours before the test on groups of 10 animals; a control group of animals to which neither compound was administered was also used.

The overall results are shown in Table II below:

TABLE II

| | Number of cramps | Percentage inhibition relative to the control animals |
|---|---|---|
| Control | 449 | |
| Injectable aspirin, 50 mg/kg (expressed as acetylsalicylic acid) | 386 | −14% |
| Injectable aspirin, 100 mg/kg (expressed as acetylsalicylic acid) | 196 | −56% |
| Compound according to the invention, 50 mg/kg (expressed as weight of compound) | 396 | −12% |
| Compound according to the invention, 100 mg/kg (expressed as weight of compound) | 194 | −57% |

These results show that 1-o-acetoxybenzoyl-4-hydroxy-L-proline, which has, for the same weight, an acetylsalicylic acid content which is half that of the injectable aspirin, exhibits an activity which is practically twice that of the injectable aspirin.

EXAMPLE 4

Anti-inflammatory activity

The anti-inflammatory activity of 1-o-acetoxybenzoyl-4-hydroxy-L-proline was studied by means of the carrageenin-induced plantar oedema test on rats.

One pair of each rat in three groups of 8 to 9 rats was injected with carrageenin at time Ho. The first group was a control group and the second and third groups were test groups. The volume ($V_1$) of the paw was then measured, and the compounds to be tested were administered intraperitoneally. The volume ($V_2$) of the same paw was measured again three hours later.

By way of comparison, the same injectable aspirin as that used in Examples 2 and 3 above was also tested.

The results, expressed as a percentage variation in volume, i.e. $(V_2 - V_1)/V_1 \times 100$, are shown in Table III below:

TABLE III

| Controls | Injectable aspirin, 200 mg/kg (expressed as weight of compound) | Compound according to the invention, 200 mg/kg (expressed as weight of compound) |
|---|---|---|
| 105% | 87.5% | 63.5% |
| 89.2% | 74.4% | 61.6% |
| 100% | 61% | 67.4% |
| 74.4% | 85% | 53.7% |
| 85.4% | 64% | 60.9% |
| 76% | 74.4% | 63.6% |
| 89.8% | 83.3% | 64% |
| 86% | 70.7% | 82.5% |
| | 68.3% | 82.3% |
| X̄ 88.22% ± 10.5 | 74.29% ± 9.36 | 66.61 ± 9.7 |
| Percentage variation | −16% | −24% |
| P: | >0.02 | >0.001 |

The results in Table III above show that 1-o-acetoxybenzoyl-4-hydroxyl-L-proline exhibits very good anti-inflammatory activity, markedly superior to that of the injectable aspirin.

EXAMPLE 5

Antipyretic activity

The antipyretic activity of 1-o-acetoxybenzoyl-4-hydroxyl-L-proline was assessed by the hyperthermia caused by the injection of brewer's yeast 17 hours before the start of the experiment (groups of 8 rats + 1 comparison group without yeast). The first temperature measurement was made at time Ho and the compounds to be tested were then administered intraperitoneally. The central temperature was then checked 1 hour 30 minutes, 3 hours and 4 hours 30 minutes after Ho.

The overall results are shown in Table IV below:

TABLE IV

| | Ho °C | 1 hr 30 mins °C | 3 hrs °C | 4 hrs 30 mins °C |
|---|---|---|---|---|
| 40 animals + yeast, at Ho | 37.28 ± 0.052 | | | |
| Injectable aspirin 200 mg to 400 mg/kg | | 36.64 ± 0.19 | 36.92 ± 0.09 | 36.90 ± 0.12 |
| Compound according to the invention, 200 mg to 400 mg/kg | | 36.12 ± 0.25 | 36.40 ± 0.14 | 36.82 ± 0.11 |

The results show that the antipyretic activity of 1-o-acetoxybenzoyl-4-hydroxy-L-proline was greater than that of the injectable aspirin.

EXAMPLE 6

Preparation of 1-o-acetoxybenzoyl-L-proline 53.7 g (0.27 mol) of o-acetoxybenzoyl chloride in 100 ml of anhydrous ethyl ether and 37.8 ml (0.27 mol) of pure triethylamine in 250 ml of iced water were added simultaneously to a solution of 31.2 g (0.27 mol) of L-proline in 90 ml of water and 37.8 ml (0.27 mol) of pure triethylamine over the course of half an hour, at −2° ± 1° C., whilst stirring so as to produce emulsification.

Stirring was continued for 1 hour at the same temperature; the reaction mixture was allowed to return to ambient temperature over the course of 1 hour, and was kept at ambient temperature for half an hour.

The pH was reduced from 6 to 2 by adding 23.7 ml of 11.6 N hydrochloric acid. The milky cloudiness was extracted successively with 125 ml, 65 ml (twice) and then 35 ml of pure methylene chloride and the extracts were dried over anhydrous $Na_2SO_4$ and gradually evaporated in vacuo under anhydrous conditions until the bath temperature was 120° C., in order to drive off the solvent and the fixed water. The residue (65.7 g) was dissolved in 50 ml of anhydrous methylene chloride, 50 ml of ether, followed by 50 ml of anhydrous hexane, and the mixture was seeded and left to crystallise.

The mother liquors were decanted and the crystals were washed several times with anhydrous ether. The product was recrystallised by dissolving it in 80 ml of methylene chloride and then adding an equal amount of hexane, both these solvents being anhydrous.
Yield: — 30–34 g (40–45% of the theoretical yield)
Melting point: — 136° C. (hygroscopic product)
Solubility in water: — 5%
Elementary analysis:
Calculated %: C = 60.64; H = 5.45; N = 5.05; O = 28.85
Found %: C = 60.30; H = 5.53; N = 5.30; O = 29.36

EXAMPLE 7

Anti-inflammatory activity

The anti-inflammatory activity of 1-o-acetoxybenzoyl-L-proline was studied by means of the carrageenin-induced oedema test on rats. In this test, the antiinflammatory activity of the compound according to the invention was compared with that of an injectable aspirin, namely lysine acetylsalicylate.

the compounds were injected intramuscularly, 30 minutes before the carrageenin. The volume of the oedema was measured three hours afterwards.

The results are shown in Table V below; from this table it will be seen that 1-o-acetoxybenzoyl-L-proline exhibits, at a dose of 100 mg, an antiinflammatory activity comparable to that of lysine acetylsalicylate used at medium doses.

TABLE V

| | Dose mg/kg | Number of rats | % Variation in the volume of the oedema | % inhibition |
|---|---|---|---|---|
| Comparisions | | 26 | 107.39 ± 5.19 | |
| Lysine acetyl-salicylate | 50 | 8 | 89.41 ± 9.39 | 16.74 |
| | 100 | 8 | 77.79 ± 5.39 | 27.56 |
| | 200 | 8 | 62.54 ± 6.83 | 41.76 |
| 1-o-acetoxybenz-oyl-L-proline | 50 | 10 | 104.73 ± 7.23 | 2.48 |
| | 100 | 10 | 81.65 ± 5.97 | 23.97 |
| | 200 | 10 | 75.71 ± 4.8 | 29.50 |

EXAMPLE 8

Analgesic activity

The analgesic activity of 1-o-acetoxybenzoyl-L-proline was studied on rats by means of the Randall-Selitto test (Arch. int. Pharmacodyn., 1957, 111, 409, 419).

The results are shown in Table VI below; from this table, it will be seen that 1-o-acetoxybenzoyl-L-proline exhibits, at a dose of 100 mg, an analgesic activity comparable to that of lysine acetylsalicylate used at medium doses.

TABLE VI

| | Dose mg/kg | Number of rats | Inhibition % | | |
|---|---|---|---|---|---|
| | | | 1 hour | 2 hours | 4 hours |
| Lysine acetylsalicylate | 50 | 10 | 72.98 ±2.26 | 60.26 ±8.38 | 65.79 ±8.82 |
| | 100 | 10 | 85.14 ±14.39 | 97.44 ±14.07 | 73.68 ±10.71 |
| | 200 | 10 | 105.40 ±19.20 | 124.36 ±10.85 | 111.84 ±11.51 |
| 1-o-acetoxybenz-oyl-L-proline | 50 | 10 | 59.49 ±10.02 | 67.57 ±11.25 | 44.00 ±12.69 |
| | 100 | 10 | 74.68 ±12.34 | 89.19 ±14.24 | 53.33 ±14.91 |
| | 200 | 10 | 98.73 ±16.45 | 130.98 ±16.94 | 104.01 ±19.88 |

We claim:
1. 1-(o-acetoxybenzoyl)-L-prolines of the formula:

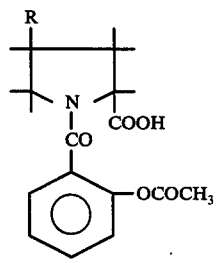

where R is H or OH.

2. An analgesic, anti-inflammatory or antipyretic composition in dosage unit form consisting of from 100 mg to 1 g of a compound of claim 1 and a pharmaceutical carrier.

* * * * *